United States Patent [19]

Murr

[11] Patent Number: 4,558,933

[45] Date of Patent: Dec. 17, 1985

[54] METHOD AND APPARATUS FOR UNIFORM BACKGROUND IN VISUAL FIELD TESTING DEVICES

[75] Inventor: William C. Murr, Piedmont, Calif.

[73] Assignee: Bausch & Lomb Incorporated, Rochester, N.Y.

[21] Appl. No.: 499,313

[22] Filed: May 31, 1983

[51] Int. Cl.⁴ .............................................. A61B 3/02
[52] U.S. Cl. ..................................... 351/226; 351/224
[58] Field of Search ........................ 351/224, 225, 226

[56] References Cited

U.S. PATENT DOCUMENTS 4,063,807 12/1977 Gelius et al. ........................ 351/226

4,392,725 7/1983 Sheingorn ........................... 351/224

Primary Examiner—Rodney B. Bovernick
Attorney, Agent, or Firm—Bernard D. Bogdon

[57] ABSTRACT

A method and apparatus for providing a uniform testing field for visual field mapping includes a concave viewing screen and a plurality of selectively illuminated test points spaced thereabout. A testing device selects test points randomly and sequentially and records a subject response to map the visual field. Those test points not selected at any given time are strobed with a pulse intensity, duration, and repetition rate to render the test points equal in luminance to the surrounding background areas of the screen.

17 Claims, 1 Drawing Figure

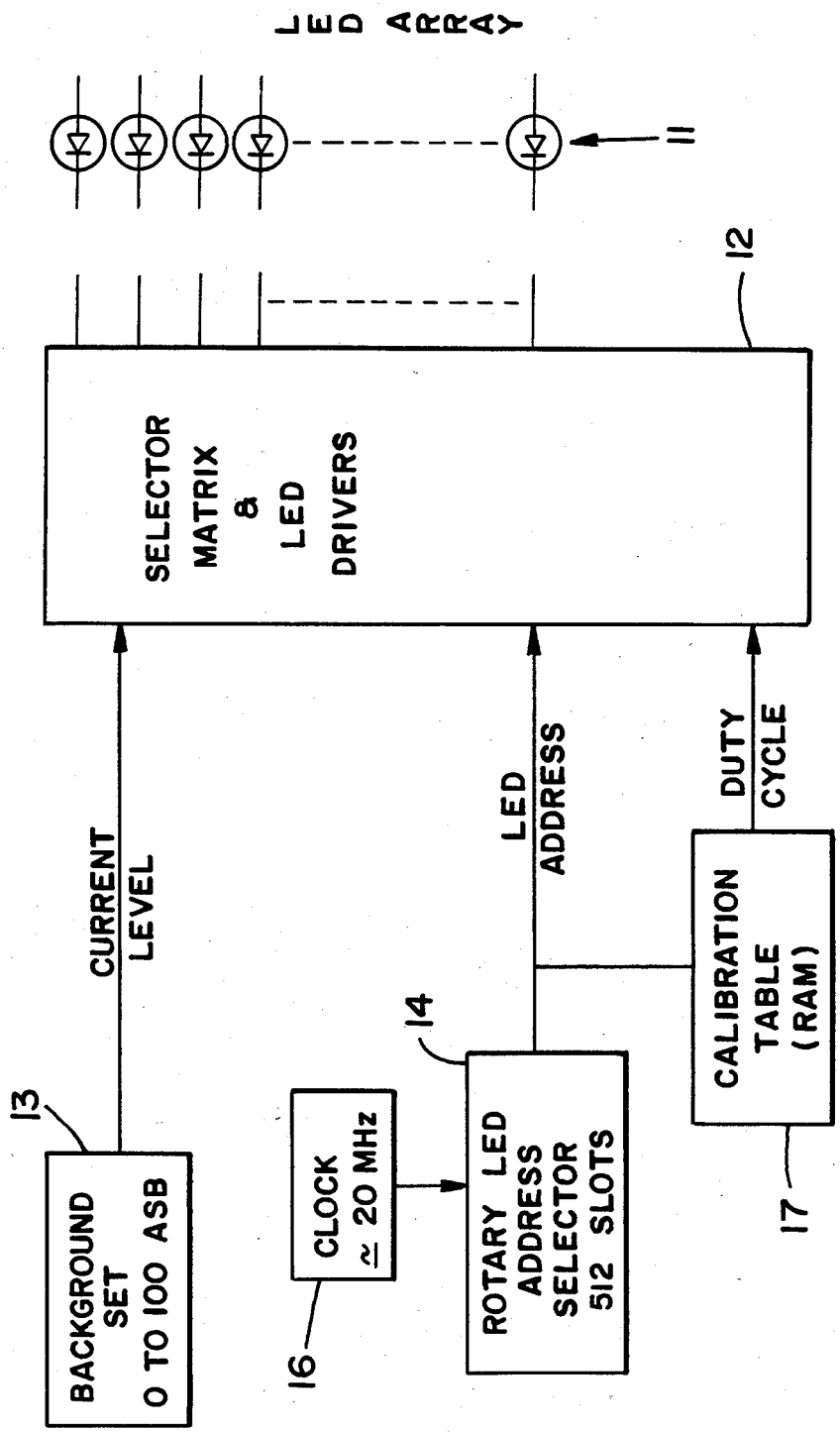

METHOD AND APPARATUS FOR UNIFORM BACKGROUND IN VISUAL FIELD TESTING DEVICES

BACKGROUND OF THE INVENTION

Until recent years the mapping of the shape of the visual response field of an individual involved crude techniques that rendered the results fraught with imprecision and inaccuracies. This visual field mapping was of limited utility in medical diagnosis, especially regarding diseases of the eye and brain.

However, with the advent of modern visual field mapping devices, the visual field can be mapped accurately and precisely. As a result this technique has become an important diagnostic tool. These devices provide a concave screen on which a large plurality of test points are disposed. The test points may comprise individual LED's, or may be joined to the end of an individually illuminated light conducting fiber. The test points are randomly and sequentially illuminated, and the subject's response is recorded automatically on a chart or other permanent record. The luminance of the screen and of the illuminated test points are controlled at all times so that a mapping procedure may be repeated with a great deal of accuracy. Thus small changes in the subject's visual field may be detected, and related diseases may be diagnosed earlier. One exemplary device is described in U.S. Pat. No. 4,146,311, issued to William C. Murr on Mar. 27, 1979.

One minor problem in visual field testing is that the test points disposed about the screen may not have the same luminance as the screen itself. This situation may arise because the LED's or optical fiber ends may reflect less of the light illuminating the screen (when they are not actuated). As a result the subject actually has an effective stimulus which is greater than would be experienced if these areas were of uniform luminance with the surrounding screen. That is, the subject sees the test points as dark spots which become lighted when actuated, rather than seeing a completely neutral field in which points of light appear randomly. This effect is most noticeable at low stimulus values.

SUMMARY OF THE PRESENT INVENTION

The present invention generally comprises a method and an apparatus for providing a testing field for visual field mapping which is completely uniform in appearance. That is, the present invention provides a means for assuring that the test points in the field mapping device have the same luminance as the background formed by the viewing screen.

A typical visual field testing and mapping device generally includes a concave viewing screen and a plurality of selectively illuminated test points spaced thereabout. The testing device selects test points randomly and sequentially and records a subject response to map the visual field. According to the present invention, those test points not selected and not actuated at any given time are strobed with a pulse intensity, duration, and repetition rate to render the test points equal in luminance to the surrounding background areas of the screen. The pulse frequency, duration, and intensity can be altered according to a lookup table stored in a memory device, so that the test points can be made to equal the screen luminance in a wide range of background illumination.

BRIEF DESCRIPTION OF THE DRAWING

The FIGURE is a block diagram of the circuitry of the apparatus of the present invention.

DESCRIPTION OF THE PREFERRED EMBODIMENT

The present invention generally comprises a method and an apparatus for achieving a uniform testing field in a visual field mapping device. More specifically, the invention provides for partial illumination of the test points which are not actuated, so that the luminance of the test points matches the selectively variable background luminance. This partial illumination is achieved by strobing the unactuated test points with pulses of selected duty cycle and intensity to equalize the luminance of the test points and the background screen.

With reference to the accompanying Figure, the present invention is described in relationship to a visual field mapping device which employs a plurality of LED test points 11. The test points are arrayed about a concave background screen which is selectively illuminated by a controlled, variable light source. A means for providing a controlled, variable background illumination is described in the aforementioned Murr patent, and includes a controlled current source 13 which is connected to operate a background illumination lamp. All of the LED's 12 are connected to a selector matrix and LED driver circuit 12. Each of the LED's 11 is connected to a driver in the circuit 12, and the circuit 12 also includes a logic array which permits addressing of any one of the LED's 11 through its associated driver.

The apparatus also includes an LED address selector 14 which is connected to deliver LED addresses to the circuit 12 in sequential fashion. Although in the illustrated embodiment the address selector 14 comprises a rotary selector having 512 address slots, it may be appreciated that the addresses may be selected from a predetermined order stored in a memory device, or by other techniques known in the prior art. The address selector is also connected to a clock 16 which provides timing pulses to the selector 14.

The LED address from the address selector 14 is also delivered to a calibration table 17. The calibration table comprises a memory device such as a random access memory or a read only memory in which there is stored data relating the address of each LED and the duty cycle corresponding to a desired luminance level for that particular test point. This duty cycle information is retrieved from the table whenever any LED is selected for actuation and is fed to the selector matrix 12 so that as each test point is actuated in sequence, the effective luminance of the test point is controlled to be equal to a predetermined level. This effect is achieved by pulsing the selected LED for approximately 10 microseconds, followed by a a variable off period. The length of the deactuated period determines the effective luminance of the LED, as does the current level fed to the LED during the actuation period. The LED must be pulsed at a repetition rate greater than approximately 60 Hz, so that the human flicker frequency perception threshold is exceeded.

As described previously, the background illumination adjustment 13 includes a controlled current source which operates the background illumination lamp. This current level is also connected to the selector matrix 12 to provide a current level for the strobed actuation of all of the LED's which are not selected at any given time.

The non-selected LED's are strobed sequentially for approximately 10 microseconds each, the pulses being repeated at a rate greater than the 60 Hz flicker fusion threshold. The strobe rate may be set by the rate provided by the calibration table 17, or may be derived directly from the clock 16.

It may be appreciated that illuminating all of the non-selected LED's with a constant low level DC current would achieve the same desired result of eliminating the dark spot stimuli of the test points. However, this technique would require a very large total current, and would exceed the capacity of a large regulated power supply. The strobe technique of the present invention, on the other hand, provides matching luminance between the test points and the background screen, and requires a total current comsumption far less than would constant illumination. The current level from the background set device 13 attenuates the effective luminance of the strobed, non-selected LED's in correspondence with the actual screen luminance, so that the strobe duty cycle of the non-selected LED's need not be calibrated, but should finer accuracy seem desirable, individual adjustment may be made for each non-selected LED by reference to the calibration table. Either approach is feasible within the time constraints encountered in practice.

I claim:

1. A device for providing a uniform testing field for a visual field mapping device which includes a concave viewing screen and a plurality of selectively illuminated test points spaced thereabout, comprising:
   means for illuminating said viewing screen at a selectively variable luminance level;
   means for sequentially selecting and illuminating said test points to determine the visual response of a subject; and
   means for strobing the test points not currently selected by said means for sequentially selecting at a rate and intensity so that the luminance of the non-currently selected test points is substantially equal to the screen luminance.

2. The device of claim 1, wherein said means for illuminating said viewing screen includes a controlled, selectively variable current source for driving a screen illumination device, and means for connecting said controlled current source to said means for strobing the to produce strobe pulses having a magnitude proportional to the current level from said controlled current source.

3. The device of claim 1, wherein said test points comprise a plurality of LED's, and said means for sequentially selecting said test points includes means for strobing the selected test points at a rate greater than approximately 60 Hz.

4. The device of claim 1, wherein said means for strobing includes means for sequentially strobing said non-currently selected test points.

5. The device of claim 4, wherein said non-currently selected test points are strobed sequentially for a period of approximately 10 microseconds each, and at a rate greater than 60 times per second.

6. The device of claim 3, further including calibration means for adjusting the strobe pulse duty cycle of each of said test points as they are selected to produce a predetermined effective luminance.

7. The device of claim 6, wherein said calibration means includes memory device means for storing the numerical address of each of said LED's and the appropriate duty cycles to produce said predetermined effective luminance level.

8. A method for providing a uniform testing field in a visual field mapping device which includes a concave viewing screen and a plurality of test points disposed thereabout, comprising the steps of:
   illuminating said screen at a desired luminance level with a lighting device driven by a controlled, variable current;
   sequentially selecting and illuminating said test points to determine the visual response of a subject; and
   strobing the test points not currently selected in said step of sequentially selecting at a pulse rate and duration to substantially equalize the luminance levels of such non-currently selected test points and said screen.

9. The method of claim 8, further including the step of strobing said non-currently selected test points sequentially at a rate greater than approximately 60 times per second.

10. The method of claim 8, wherein said step of strobing said non-currently selected test points includes the step of sequentially strobing said non-currently selected test points.

11. Visual field mapping apparatus having a uniform appearance, comprising:
   a concave viewing screen;
   a plurality of test points spaced about said viewing screen;
   means for sequentially selecting and illuminating said test points;
   means for illuminating said viewing screen and all of said test points at a selectively variable luminance level in such a manner that the luminance of said viewing screen is greater than the luminance of said test points; and
   means for strobing the test points not currently selected by said means for sequentially selecting at a rate and intensity sufficient to cause the luminance of such non-currently selected test points to be substantially equal to the luminance of said viewing screen.

12. The visual field mapping apparatus of claim 11, wherein said means for illuminating said viewing screen includes:
   a controlled, selectively variable current source for driving a screen illumination device; and
   means for connecting said controlled current source to said means for strobing to produce strobe pulses having a magnitude proportional to the current level from said controlled current source.

13. The visual field mapping apparatus of claim 11, wherein said test points comprise a plurality of LED's, and said means for sequentially selecting said test points includes means for strobing the selected test points at a rate greater than approximately 60 Hz.

14. The visual field mapping apparatus of claim 13, further including calibration means for adjusting the strobe pulse duty cycle of each of said test points as they are selected to produce a predetermined effective luminance.

15. The visual field mapping apparatus of claim 14, wherein said calibration means includes memory device means for storing the numerical address of each of said LED's and the appropriate duty cycles to produce said predetermined effective luminance level.

16. The visual field mapping apparatus of claim 11, wherein said means for strobing includes means for sequentially strobing said non-currently selected test points.

17. The visual field mapping apparatus of claim 16, wherein said non-currently selected test points are strobed sequentially for a period of approximately 10 microseconds each, and at a rate greater than about 60 Hz.

* * * * *

UNITED STATES PATENT AND TRADEMARK OFFICE
CERTIFICATE OF CORRECTION

PATENT NO. : 4,558,933

DATED : December 17, 1985

INVENTOR(S) : William C. Murr

It is certified that error appears in the above-identified patent and that said Letters Patent is hereby corrected as shown below:

Col. 1, line 11, "This" should read --Thus--.

Col. 2, line 46, "is" should read --are--.

Col. 3, line 44, Claim 2, delete the word "the".

Signed and Sealed this

Twenty-second Day of July 1986

[SEAL]

Attest:

DONALD J. QUIGG

Attesting Officer

Commissioner of Patents and Trademarks